(12) United States Patent
Bock et al.

(10) Patent No.: US 10,980,712 B2
(45) Date of Patent: Apr. 20, 2021

(54) PHOTOCHROMIC DENTAL MATERIAL WITH ENCAPSULATED PHOTOCHROMIC COLORANTS

(71) Applicant: Ivoclar Vivadent AG, Schaan (LI)

(72) Inventors: Thorsten Bock, Feldkirch (AT); Martina Hauner-Westphal, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 99 days.

(21) Appl. No.: 16/251,157

(22) Filed: Jan. 18, 2019

(65) Prior Publication Data

US 2019/0224080 A1 Jul. 25, 2019

(30) Foreign Application Priority Data

Jan. 23, 2018 (EP) .................................. 18152977

(51) Int. Cl.
| | |
|---|---|
| *A61K 6/66* | (2020.01) |
| *A61K 6/20* | (2020.01) |
| *A61K 6/62* | (2020.01) |
| *A61K 6/77* | (2020.01) |
| *A61K 6/78* | (2020.01) |
| *A61K 6/887* | (2020.01) |

(52) U.S. Cl.
CPC ................. *A61K 6/66* (2020.01); *A61K 6/20* (2020.01); *A61K 6/62* (2020.01); *A61K 6/77* (2020.01); *A61K 6/78* (2020.01); *A61K 6/887* (2020.01)

(58) Field of Classification Search
CPC ............. A61K 6/66; A61K 6/20; A61K 6/887

USPC ............... 523/115, 116, 117, 118; 428/402.2
See application file for complete search history.

(56) References Cited

U.S. PATENT DOCUMENTS

| | | | |
|---|---|---|---|
| 5,698,020 A | 12/1997 | Salz et al. | |
| 6,770,436 B1 | 8/2004 | Beecher et al. | |
| 2004/0194172 A1* | 9/2004 | Edge, III | ................. A01H 5/10 800/320.3 |
| 2019/0008728 A1 | 1/2019 | Moszner et al. | |

FOREIGN PATENT DOCUMENTS

| | | |
|---|---|---|
| DE | 2906193 C2 | 5/1991 |
| DE | 3220257 C2 | 2/1994 |

OTHER PUBLICATIONS

Gächter, R., et al., "Stabilizers, Auxiliaries, Plasticizers, Fillers, Reinforcing Agents, Colorants for Thermoplastics," Handbook of Plastic Additives, 3rd Edition, pp. 1-2 (translation of chapter headings for pp. 663-737), Carl Hanser Verlag, Munich Vienna, 1989.
Dürr, Dr. Heinz et al., "Photochromism: Molecules and Systems," Studies in Organic Chemistry 40, Elsevier, 1990.
Dürr, Dr. Heinz, Perspectives in Photochromism: A Novel System Based on the 1,5-Electrocyclization of Heteroanalogous Pentadienyl Anions—Dürr—1989—Angewandte Chemie Intenational Edition in English—Wiley Online Library.

(Continued)

*Primary Examiner* — Sanza L. McClendon
(74) *Attorney, Agent, or Firm* — Ann M. Knab; Thad McMurray (57) ABSTRACT

Radically polymerizable dental material, which contains at least one encapsulated photochromic colorant.

19 Claims, 3 Drawing Sheets

(56) References Cited

OTHER PUBLICATIONS

Tatiya, P. D., et al., "Novel Polyurea Microcapsules Using Dendritic Functional Monomer: Synthesis, Characterization, and Its Use in Self-healing and Anticorrosive Polyurethane Coatings," I&EC Research (Industrial & Engineering Chemistry Research), American Chemical Society, 52 (34), pp. 1562-1570, 2013.

Hedaoo, R. K., "Fabrication of dendritic 0 G PAMAM-based novel polyurea microcapsules for encapsulation of herbicide and release rate from polymer shell in different environment," Designed Monomers and Polymers, vol. 17, No. 2, pp. 111-125, Taylor & Francis Group, 2014.

Hedaoo, R. K., "Fabrication of Core-Shell Novel Polyurea Microcapsules Using Isophorone Diisocyanate (IPDI) Trimer for Release System," International Journal of Polymeric Materials and Polymeric Biomaterials, 63, pp. 352-360, 2014.

Benita, Simon, "Microencapsulation: Methods and Industrial Applications," Second Edition. Hebrew University of Jerusalem, Israel. Taylor & Francis Group, 2006.

Daz, "Spray Drying," German Pharmacist Journal, 2012.

Zhou, Y., "Preparation and application of melamine-formaldehyde photochromic microcapsules," Sensors and Actuators, vol. 188, Elsevier, 2013.

Feczko, T., "Preparation and characterization of photochromatic poly(methyl methacrylate) and ethyl cellulose nanocapsules containing a spirooxazine dye," Journal of Photochemistry and Photobiology A: Chemistry 222, pp. 293-298, 2011.

* cited by examiner

PHOTOCHROMIC DENTAL MATERIAL WITH ENCAPSULATED PHOTOCHROMIC COLORANTS

CROSS-REFERENCE TO RELATED APPLICATIONS

This application claims priority to European patent application No. 18152977.7 filed on Jan. 23, 2018, the disclosure of which is incorporated herein by reference in its entirety.

FIELD OF THE INVENTION

The present invention relates to thermally and/or light-curing dental materials with light-induced, reversible coloring, such as polymerizable resins and composites, which are particularly suitable as dental fissure sealants, filling composites, veneering materials and dental coating materials, as well as for the production of inlays and onlays.

BACKGROUND

In the case of plastic-based dental materials, colorants, a distinction being drawn between dyes and pigments, are added to the polymer as additives to set the desired color and transparency.

Dyes are organic in nature and are usually soluble in organic solvents, while pigments are solid particles with particle sizes between approx. 0.01 and approx. 1 µm and are divided into organic and inorganic pigments (cf. Taschenbuch der Kunststoff-Additive [Plastics Additives Handbook], eds. R. Gächter, H. Müller, $3^{rd}$ ed., Carl Hanser Verlag, Munich and Vienna 1989, 663-736). In the case of dental materials for dentistry and in particular in the case of highly aesthetic filling composites, mixtures of different inorganic pigments, which are characterized by low solubility in organic solvents and fats as well as by a very good color stability, are used to set the color. In addition to the permanent coloration of dental materials, it is advantageous in some situations to be able to make the dental material more visible temporarily by reversible coloring. Examples of this are a reversible coloring to detect thin layers, such as in the case of fissure sealing, of tooth surfaces treated with adhesives or of excess cement.

EP 0 744 172 A2 discloses photochromic dental materials, which contain a photochromic material such as, for example, a photochromic dye, a photochromic glass, a photochromic ceramic or a photochromic glass ceramic. The photochromic dental material can be converted into a colored state, which means it can be better distinguished from the natural hard tooth tissue, through brief irradiation with light. A disadvantage is that the subsequent decoloration sometimes takes several hours, which can impair the light-induced material curing. In addition, the dentist cannot conclusively check the final coloring of the restoration at the end of the session, with the result that another visit by the patient is necessary.

When photochromic glass fillers are used, a further difficulty is that the filler content of about 15% necessary to achieve a visible color change significantly increases the viscosity of the material, with the result that such fillers are unsuitable for applications which require a low viscosity. The relatively high filler content additionally limits the use of further fillers, e.g. the use of fluoride-releasing fillers. Another disadvantage is that photochromic glasses, the color change of which as a rule involves the use of silver halides, darken under the action of light. This darkening can be distinguished from a marginal gap or a discoloration caused by caries, e.g. when checking the retention of fissure sealants, only with difficulty, which favours misinterpretations.

On the other hand, photochromic dyes have the disadvantage that their function is impaired by the surrounding matrix. The stiffness of the matrix, the free volume, polarity and hydrophobicity, intermolecular interactions between matrix and dye and the miscibility play a role here. Interactions between matrix and dye or steric hindrance can interfere with the chemical processes of the photochromic system responsible for the color transition. This can make the desired color change very difficult or even prevent it completely. Although these disadvantages were able to be repressed by the use of flexible matrix materials with a low glass transition point $T_g$, this possibility is ruled out in the case of dental materials because the hardness and strength of the materials would be impaired by it. For the same reason, the use of porous matrix materials, which give the photochromic dye a certain molecular mobility, is also not possible.

EP 3 184 096 A1 discloses radically polymerizable dental materials with light-induced reversible coloring. The materials can be colored by brief irradiation with light with a first wavelength and decolored again by irradiation with light with a second wavelength. A disadvantage is that light sources which can emit light with different wavelengths are required, with the result that the curing lights available in dental practices cannot be used.

EP 1 230 906 A1 discloses dental materials which contain a thermochromic dye and which exhibit a reversible color change in the case of changes in temperature. This can lead to unintended coloring in hot or cold surroundings or when taking hot or cold food or drinks.

Materials with fluorescent dyes, which emit visible light when irradiated with UV light, are known from DE 39 39 998 A1. Since the fluorescence only occurs during the UV irradiation, the working area must be continuously irradiated with an additional light source, which makes its accessibility more difficult.

SUMMARY

The object of the invention is to provide photochromic materials for dental applications which do not have the disadvantages associated with the state of the art. In particular, the materials are to exhibit a clearly visible color effect, which means they can be clearly distinguished from the natural tooth tissue, they are to decolor quickly, with the result that a conclusive assessment of the coloration is possible in the course of one dental appointment, and they are to have permanently photochromic properties. A further object is the provision of photochromic dental materials with low viscosity which are particularly suitable as fissure sealants. The materials are to be capable of being used with the usual equipment of a dental practice.

BRIEF DESCRIPTION OF THE DRAWINGS

Further advantages, details and features result from the following description of several examples of profiles in accordance with the invention, while reference is made to the drawings, wherein.

DETAILED DESCRIPTION

The object is achieved according to the invention by radically polymerizable dental materials which contain at least one encapsulated photochromic colorant.

By encapsulated colorants is meant colorants which are encased in a polymer capsule. In contrast to polymer particles, the polymer capsules are not solid but have an outer capsule wall and an inner core. The core of the capsules can be solid, gaseous or preferably liquid. The core contains the colorant in dissolved or dispersed form. The colorant is preferably present in chemically unbonded form.

The capsule wall is preferably formed by an organic polymer. Polymers based on melamine-formaldehyde resins, polyurethanes, polysaccharides, urea-formaldehyde resins, polymethacrylates and polylactic acid are preferred. Polymers based on melamine-formaldehyde resins are particularly preferred, wherein melamine-formaldehyde resin based on N-(4,6-diamino-1,3,5-triazin-2-yl)formamide (CAS No. 13236-84-5) is quite particularly preferred. In the case of melamine-formaldehyde resins, the capsule wall is formed by polycondensation.

The capsules contain at least one photochromic colorant, preferably at least one photochromic organic dye or a photochromic organic pigment. According to the invention, photochromic colorants are preferred which exhibit a color change when irradiated with light and which subsequently decolor again thermally.

Suitable photochromic dyes are described, for example, in Photochromism—Molecules and Systems (Dürr, H.; Bouas-Laurent, H., editors, Elsevier, 1990). Preferred photochromic dye systems are based on the cis/trans-isomerism of azobenzene compounds or stilbenes, the interconversion or electrocyclic ring-closing or ring-opening reaction of spiropyran systems or spirooxazines to form merocyanines, or the 1,5-electrocyclization of pentadienyl anions.

A preferred group of photochromic dyes are spiro[1,8a-indolizine] derivatives, in particular spiro[1,8a-dihydroindolizine] and spiro[1,8a-tetrahydroindolizine] derivatives. Suitable derivatives and processes for the preparation thereof are disclosed, for example, in DE 29 06 193 C2 and DE 32 20 257 C2.

Systems which are based on a 1,5-electrocyclization, such as are described by H. Dürr in Angew. Chem. 101 (1989), pages 427 to 445 in chapter 3, are further preferred.

Spiro[fluorene-9,1'[1,8a]dihydroindolizine] derivatives, in particular derivatives according to Formula I as defined in EP 0 744 172 A2, are likewise preferred.

Particularly preferred photochromic dyes are spirooxazines, in particular those with the parent substance 1,3,3-trimethyl-spiro[indoline-2,3'-[3H]naphtho[2,1-b][1,4] oxazine (NISO). A quite particularly preferred dye of this type is 6'-piperidine-1,3,3,-trimethyl-spiro[indoline-2,3'-[3H]naphtha[2,1-b]-[1,4]oxazine] (CAS No. 114747-45-4; Reversacol Plum Red).

The photochromic dyes used according to the invention are characterized by a reversible, light-induced coloring, i.e. they can be colored by brief irradiation with light with the wavelength $\lambda_1$, and, under physiological conditions such as exist, e.g., in the oral cavity, they decolor through a thermally induced back reaction after completion of the irradiation.

The reactions taking place are shown by way of example for dyes with the NISO parent substance:

The uncolored compounds are characterized by a closed ring (left-hand formula), the colored compounds by an open ring (right-hand formula). The materials according to the invention are preferably sold in the uncolored form, and the photochromic dyes are accordingly defined here using the formulae for the uncolored compounds. However, it is self-evident that those materials which contain the corresponding colored compounds are also a subject-matter of the invention.

According to the invention, those photochromic dyes which can be activated with light with a wavelength $\lambda_1$ of from 350 to 800 nm, preferably 370 to 490 nm, particularly preferably 370 to 470 nm and quite particularly preferably with light with a wavelength in the range of from 415 to 465 nm, are preferred. This makes it possible to use dental curing lights customary in the trade to activate the color change. Here, dyes which have no, or only a little, inherent color in the unactivated state are particularly preferred.

In addition, it is preferred that, in the colored state, the dental materials according to the invention have a high-contrast color in comparison with the hard tooth tissue and with any caries present. Dyes which are colored red, pink, green or blue in the activated state, and can be distinguished well from the black, brown and grey shades prevailing in the case of caries, are therefore preferred. The color shade can be set by the selection and/or combination of suitable dyes.

The core of the capsules is preferably liquid, i.e. the inside of the capsules contains a liquid, in which the photochromic colorant(s) is/are dispersed or dissolved. The liquid is preferably selected from organic solvents, particularly preferably from carboxylic acid esters. The esters of alkanols and glycerol esters are preferred. Particularly preferred glycerol esters are esters with fatty acids, which have 6 to 18 carbon atoms, particularly preferably 8 to 16 and quite particularly preferably 10 to 16 carbon atoms, wherein fatty acids with an even number of carbon atoms, such as in Miglyol (mixed decanoyl and octanoyl glycerides) and in particular glycerol tricaprylate (trioctanoin, CAS No. 538-23-8), as well as mixtures thereof, are preferred. Miglyol and trioctanoin are quite particularly preferred.

Particularly preferred alkanol esters are esters of $C_1$-$C_8$, preferably $C_1$-$C_6$ and particularly preferably $C_1$-$C_3$ alkanols with fatty acids, which have 6 to 22 carbon atoms, particularly preferably 8 to 20 and quite particularly preferably 10 to 18 carbon atoms, wherein fatty acids with an even number of carbon atoms, such as capric acid, lauric acid, myristic acid, palmitic acid and in particular stearic acid are particularly preferred. Accordingly, the esters of $C_1$-$C_3$ alkanols with $C_{10}$-$C_{18}$ fatty acids, as well as mixtures thereof, are quite particularly preferred. A particularly preferred ester is methyl stearate.

The kinetics of the photochromic reaction can be influenced by the choice of the liquid inside the capsule casing. Relevant parameters in the selection of the liquid are, e.g., polarity, hydrophobicity and the solubility or dispersibility of the dye in the liquid. In capsules with a liquid core, a photochromic behaviour can be achieved which corresponds to that of the colorant in solution. The liquid core gives the photochromic dye the necessary space required for the light-induced transition from the uncolored into the colored form and the thermal back reaction, and thus prevents limitations of the photochromic kinetics through the surrounding matrix.

The capsules can be produced by means of mechanical, physical, physico-chemical or chemical processes in a manner known per se. Suitable mechanical processes are, e.g., spray drying or coating in a fluidized bed. Suitable physical or physico-chemical processes are coacervation as well as solvent vaporization and solvent diffusion processes. Interfacial polymerization, interfacial cross-linking and in situ polymerization are suitable, e.g., as chemical processes.

Suitable processes are already known from the state of the art, such as, for example, R. J. Marathe, A. B. Chaudhari, R. K. Hedaoo, D. Sohn, V. R. Chaudhari, V. V. Gite, Urea formaldehyde (UF) microcapsules loaded with corrosion inhibitor for enhancing the anti-corrosive property of acrylic-based multifunctional PU coatings, RSC Advances, 5, 15539-15546, 2015;

Tatiya, P. D.; Gite, V. V. (2013). "Novel Polyurea Microcapsules Using Dendritic Functional Monomer: Synthesis, Characterization, and Its Use in Self-healing and Anticorrosive Polyurethane Coatings". Industrial & Engineering Chemistry Research. 52 (4): 1562-1570;

Hedaoo, R. K.; Tatiya, P. D.; Mahulikar, P. P.; Gite, V. V. (2013). "Fabrication of Dendritic OG PAMAM-Based Novel Polyurea Microcapsules for Encapsulation of Herbicide and Release Rate from Polymer Shell in Different Environment". Design Monomers and Polymers. 2014 (2): 111-125;

Hedaoo, Rahul K., et al. "Fabrication of Core-Shell Novel Polyurea Microcapsules Using Isophorone Diisocyanate (IPDI) Trimer for Release System." International Journal of Polymeric Materials and Polymeric Biomaterials 63.7 (2014) 352-360;

Simon Benita (editor), Microencapsulation: Methods and Industrial Applications (Drugs and the Pharmaceutical Sciences), CRC Press, Taylor & Francis Group, Boca Raton 2006.

Deutsche Apotheker Zeitung 16/2012, "Sprühtrocknung—so schnell kann Trocknen gehen! Von der Wirkstofflösung zum feinen Pulver" [Spray drying—drying can be this quick! From the active ingredient solution to a fine powder], https://www.deutsche-apotheker-zeitung.de/daz-az/2012/daz-16-2012/spruehtrocknung-so-schnell-kann-trocknen-gehen.

Capsule material, wall thickness and production process are preferably chosen such that capsules with a flexible casing are obtained. Electron micrographs reveal an advantageous flexibility in that the edges of the ground encapsulation lie wrinkled and flexible around the colorant (see Example 2 and FIGS. 1 and 2). The capsules preferably have a diameter of from 1 µm to 10 µm, particularly preferably from 2 µm to 8 µm, wherein the diameter was determined by measuring the capsules on SEM micrographs. The capsules preferably have a spherical shape (see FIG. 3).

Capsules which contain the photochromic dye 6'-piperidine-1,3,3,-trimethyl-spiro[indoline-2,3'-[3H]naphtho[2,1-b][1,4]oxazine] (CAS No. 114747-45-4), wherein the capsules have a wall based on melamine-formaldehyde resin (CAS No. 13236-84-5) and a liquid core, which contains trioctanoin (CAS No. 538-23-8), and wherein the dye is contained in the liquid core, are particularly preferred according to the invention.

Some encapsulated photochromic dyes that are suitable according to the invention are commercially available.

It was surprisingly found that encapsulated colorants are suitable for the production of dental materials. It was not to be expected that liquid-filled capsules would allow the production of materials which have a mechanical strength and durability after curing that is suitable for dental applications.

The dental materials according to the invention make targeted coloring or visualization by brief irradiation with light with the wavelength $\lambda_1$ possible. After completion of the irradiation, the dental materials decolor again. This process proceeds with high efficiency, even after the curing of the materials by radical polymerization.

In contrast, when unencapsulated dyes were used, a significant decrease in the duration of the color change after the polymerization was observed, i.e. the color change was only to be seen for a brief, practically insufficient period and often a color change was no longer possible. In many cases, an irreversible discoloration of the materials was observed.

It is preferred that the dental materials according to the invention decolor thermally, preferably within a period of less than 30 minutes, particularly preferably less than 5 minutes, quite particularly preferably less than 1.5 minutes and most preferably less than 1.0 minute after the activation has ended. Materials that are particularly preferred according to the invention decolor completely within 10 to 90 seconds, preferably 10 to 60 seconds.

The duration of the color change is sufficient for the visualization of fissure sealings, for checking the edges of dental restorations or for checking retention, and it allows the dentist to make a conclusive assessment of the coloration of the restoration within one treatment session.

The encapsulation of the colorants has the further advantage that the colorants can be better mixed with the other constituents which are required for the production of the dental materials. The capsules loaded with dye can be mixed directly with the other components without pre-dispersion, and a higher homogeneity is achieved. An agglomeration of the dyes in the composition was not observed. The capsules are compatible with a wide variety of matrix materials and it is not necessary to match the polymer matrix to the dyes, for example by adjusting the glass transition temperature $T_g$, such that the sought photochromic effect is achieved.

In addition, the encapsulation guarantees a high stability of the dyes, whereby the color change can be induced repeatedly over a longer period, which is advantageous in terms of subsequent check-ups.

Moreover, the encapsulation prevents the photochromic dye from being washed out of the dental material.

In addition to encapsulated photochromic dyes, the dental materials according to the invention preferably additionally contain at least one radically polymerizable monomer, in particular a mono- and/or polyfunctional (meth)acrylic acid derivative or a mixture thereof. Materials which contain at least one multifunctional (meth)acrylate or a mixture of mono- and multifunctional (meth) acrylates as radically polymerizable monomer are particularly preferred. By monofunctional (meth)acrylates is meant compounds with one, by polyfunctional (meth)acrylates is meant compounds with two or more, preferably 2 to 4, radically polymerizable groups. According to a quite particularly preferred embodiment, the compositions according to the invention contain at least one dimethacrylate or a mixture of mono- and dimethacrylates. Materials which contain mono- and multifunctional (meth)acrylates as radically polymerizable monomer are particularly suitable as dental materials. Methacrylates are preferred in all cases. It was found that the encapsulated photochromic dyes with the monomers named here are well tolerated and form homogeneous mixtures, which, when polymerized, result in materials with mechanical properties such as are desired for dental materials.

Preferred mono- or polyfunctional methacrylates are methyl, ethyl, hydroxyethyl, butyl, benzyl, tetrahydrofurfuryl or isobornyl (meth)acrylate, p-cumyl-phenoxyethylene glycol methacrylate (CMP-1E), bis-GMA (an addition product of methacrylic acid and bisphenol A diglycidyl ether), UDMA (an addition product of 2-hydroxyethyl methacrylate (HEMA) and 2,2,4-trimethylhexamethylene diisocyanate), TMX-UDMA (an addition product of a mixture of HEMA and hydroxypropyl methacrylate (HPMA) with α,α,α',α'-tetramethyl-m-xylylene diisocyanate (TMXDI)), bis(methacryloyloxymethyl)-tricycle[5.2.1.]decane (TCDMA), ethoxylated or propoxylated bisphenol A di(meth)acrylate, such as e.g. the bisphenol A dimeth-acrylate 2-[4-(3-methacryloyloxyethoxyethyl)phenyl]-2-[4-(3-meth-acryloyloxyethyl)phenyl]-propane) (SR-348c) with 3 ethoxy groups or 2,2-bis[4-(2-(meth)acryloxypropoxy)phenyl]propane, di-, tri- or tetraethylene glycol di(meth)acrylate, trimethylolpropane tri(meth)acrylate, pentaerythritol tetra(meth)acrylate, as well as glycerol di(meth)acrylate, 1,4-butanediol di(meth)acrylate, 1,10-decanediol di(meth)acrylate, 1,12-dodecanediol di(meth)acrylate or glycerol trimethacrylate (GTMA).

In addition, non-acidic esters of phosphoric acid with hydroxymethacrylates are preferred as radically polymerizable monomers. The esters of ω-hydroxy-$C_2$-$C_{10}$-alkyl methacrylates are particularly preferred. Quite particularly preferred examples are tris[2-(methacryloyloxy)ethyl] phosphate, cially available bisacrylamides, such as methylene- or ethylenebisacrylamide, or bis(meth)acrylamides, such as e.g. N,N'-diethyl-1,3-bis(acrylamido)-propane, 1,3-bis(methacrylamido)-propane, 1,4-bis(acrylamido)-butane or 1,4-bis (acryloyl)-piperazine, which can be synthesized by conversion from the corresponding diamines with (meth)acrylic acid chloride. These monomers are characterized by a high hydrolytic stability and are particularly suitable as cross-linking monomers.

The materials according to the invention preferably do not contain any acid group-containing monomers, such as carboxylic acids, phosphonic acids or sulphonic acids.

The dental materials according to the invention preferably also contain an initiator for the radical polymerization, particularly preferably a photoinitiator.

To initiate the radical photo polymerization, benzophenone, benzoin and derivatives thereof or α-diketones or derivatives thereof, such as 9,10-phenanthrenequinone, 1-phenyl-propane-1,2-dione, diacetyl or 4,4'-dichlorobenzil are preferred. Camphorquinone and 2,2-dimethoxy-2-phenyl-acetophenone are particularly preferably used and α-diketones are particularly preferably used in combination with amines as reducing agent, such as e.g. 4-(dimethylamino)benzoic acid ethyl ester, N,N-dimethylaminoethyl methacrylate, N,N-dimethyl-sym.-xylidine or triethanolamine. Norrish type I photoinitiators, above all acyl- or bisacylphosphine oxides, monoacyltrialkyl- or diacyldi-alkylgermanium compounds, such as e.g. benzoyltrimethylgermanium, dibenzoyldiethylgermanium or bis(4-methoxy- N-mono- or disubstituted acrylamides, such as e.g. N-ethylacrylamide, N,N-dimethylacrylamide, N-(2-hydroxyethyl)-acrylamide or N-methyl-N-(2-hydroxyethyl) acrylamide, or N-mono-substituted methacrylamides, such as e.g. N-ethylmethacrylamide or N-(2-hydroxyethyl) ethacrylamide as well as N-vinylpyrrolidone are further preferred. These monomers are characterized by a low viscosity and a high hydrolytic stability and are particularly suitable as diluting monomers.

Likewise preferred are cross-linking pyrrolidones, such as e.g. 1,6-bis(3-vinyl-2-pyrrolidonyl)-hexane or commerbenzoyl)di-ethylgermanium are also particularly suitable. Advantageously, mixtures of the different photoinitiators can also be used, such as e.g. dibenzoyldiethylgermanium in combination with camphorquinone and 4-dimethylaminobenzoic acid ethyl ester.

As initiators for a polymerization carried out at room temperature, redox initiator combinations are preferably used, such as e.g. combinations of benzoyl peroxide with N,N-dimethyl-sym.-xylidine or N,N-dimethyl-p-toluidine. In addition, redox systems consisting of peroxides or hydroperoxides and such reducing agents as e.g. ascorbic acid, barbiturates, thioureas or sulphinic acids are also particularly suitable.

Furthermore, the dental materials according to the invention preferably also contain at least one organic or particularly preferably inorganic particulate filler. Fillers based on oxides, such as $SiO_2$, $ZrO_2$ and $TiO_2$ and mixed oxides of $SiO_2$, $ZrO_2$, ZnO and/or $TiO_2$, nanoparticulate or microfine fillers, such as fumed silica or precipitated silica (weight-average particle size of 10-1000 nm), as well as minifillers, such as quartz, glass ceramic or X-ray-opaque glass powders of e.g. barium or strontium aluminium silicate glasses (weight-average particle size of 0.2-10 μm) are preferred. Further preferred fillers are X-ray-opaque fillers, such as ytterbium trifluoride or nanoparticulate tantalum(V) oxide or barium sulphate or mixed oxides of $SiO_2$ with ytterbium (III) oxide or tantalum(V) oxide (weight-average particle size of 10-1000 nm).

To improve the bond between the filler particles and the crosslinked polymerization matrix, $SiO_2$-based fillers can be surface-modified with methacrylate-functionalized silanes, such as e.g. 3-methacryloyloxypropyltrimethoxysilane. For the surface modification of non-silicate fillers, e.g. of $ZrO_2$ or $TiO_2$, functionalized acidic phosphates, such as e.g. 10-methacryloyloxy dihydrogen phosphate can also be used.

Depending on the desired intended use, the dental materials according to the invention can preferably also contain a solvent, in particular water, ethanol or a mixture thereof.

In addition, the materials according to the invention can contain further additives, above all stabilizers, such as e.g. polymerization stabilizers, flavouring agents, colorants, microbiocidal active ingredients, fluoride-ion-releasing additives, optical brighteners, fluorescent agents, plasticizers and/or UV absorbers.

According to the invention, those dental materials which contain the following components are preferred:
a) 0.0001 to 5 wt.-%, preferably 0.001 to 3.0 wt.-% and particularly preferably 0.1 to 1.0 wt.-% of at least one encapsulated photochromic colorant,
b) 0.01 to 10 wt.-%, particularly preferably 0.1 to 3.0 wt.-% of at least one initiator for the radical polymerization, and
c) 5 to 85 wt.-%, preferably 10 to 60 wt.-% and particularly preferably 15 to 50 wt.-% of at least one radically polymerizable monomer.

In addition, the materials according to the invention optionally contain
d) 2.50 to 80 wt.-% filler(s) and/or
e) 2.50 to 70 wt.-% solvent.

Unless otherwise stated, all quantities relate to the total mass of the dental material.

The photochromic dye content is primarily geared to the desired color effect.

Dental materials for use as fissure sealant preferably contain the following components:
a) 0.0001 to 5 wt.-%, preferably 0.001 to 3.0 wt.-% and particularly preferably 0.1 to 1.0 wt.-% of at least one encapsulated photochromic colorant,
b) 0.01 to 10 wt.-%, particularly preferably 0.1 to 3.0 wt.-% of at least one initiator, and
c) 5 to 85 wt.-%, preferably 10 to 60 wt.-% and particularly preferably 15 to 50 wt.-% of at least one monomer.

In addition, the fissure sealants according to the invention can optionally contain
d) 2.50 to 80 wt.-% filler(s) and/or
e) 2.50 to 70 wt.-% solvent.

Those materials which consist of the named components are particularly preferred in each case. Furthermore, those materials in which the individual components in each case are selected from the above-named preferred and particularly preferred substances are preferred.

The materials according to the invention are particularly suitable as dental materials, in particular as dental fissure sealants, dental cement, dental filling composite or dental veneering material. They are characterized by reversible photochromic properties.

The dental materials are suitable primarily for intraoral application by the dentist for the prophylactic sealing of fissures, but also for the restoration of damaged teeth, i.e. for therapeutic application, e.g. as dental cements, filling composites and veneering materials. However, they can also be used extraorally, for example in the production or repair of dental restorations, such as prostheses, artificial teeth, inlays, onlays, crowns and bridges.

Figure 1:
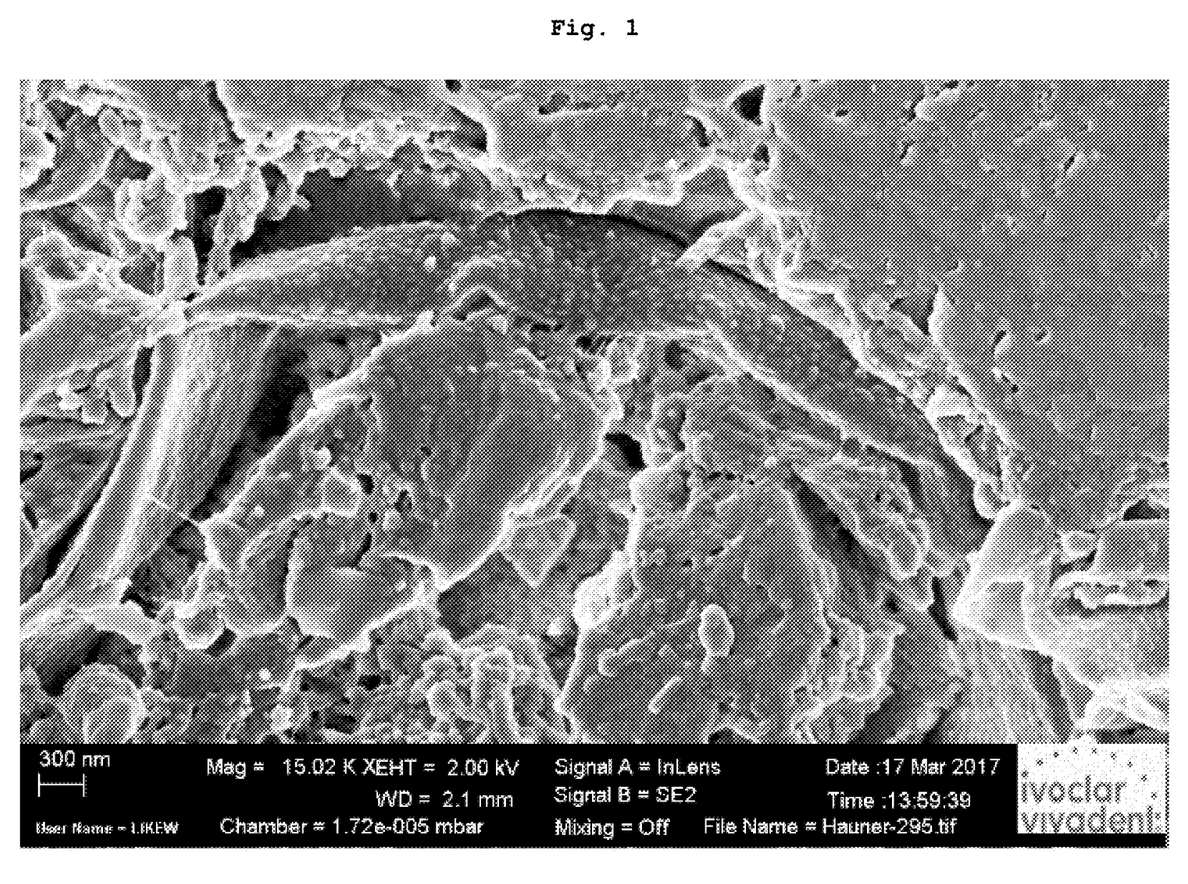
FIG. 1 shows an SEM micrograph of the edge of the casing of a ground capsule on the surface of a platelet made of a fissure sealant according to the invention.

In FIG. 1, the SEM micrograph shows the edge of the casing of a ground capsule on the surface of a platelet made of a fissure sealant according to the invention after the curing of the platelet and after the grinding of the platelet surface. The edges of the capsule wall lie wrinkled and flexible around the photochromic dye.

Figure 2:
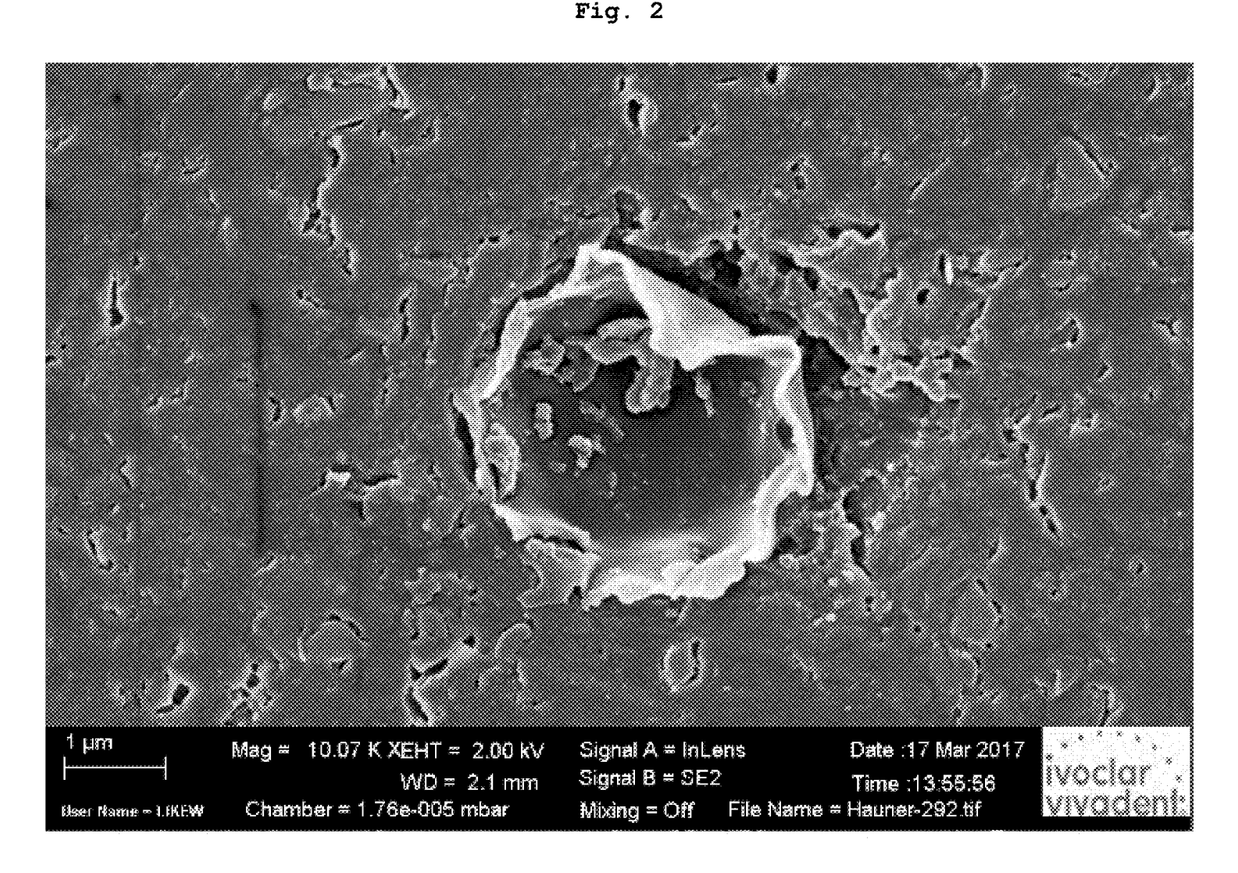
FIG. 2 shows an SEM micrograph of an empty capsule casing on the surface of the platelet.

In FIG. 2, the SEM micrograph shows an empty capsule casing on the surface of the platelet. The edges of the capsule wall lie wrinkled and flexible around the edge of the cured fissure sealant.

The micrographs show that the capsule wall is flexible.

Figure 3:
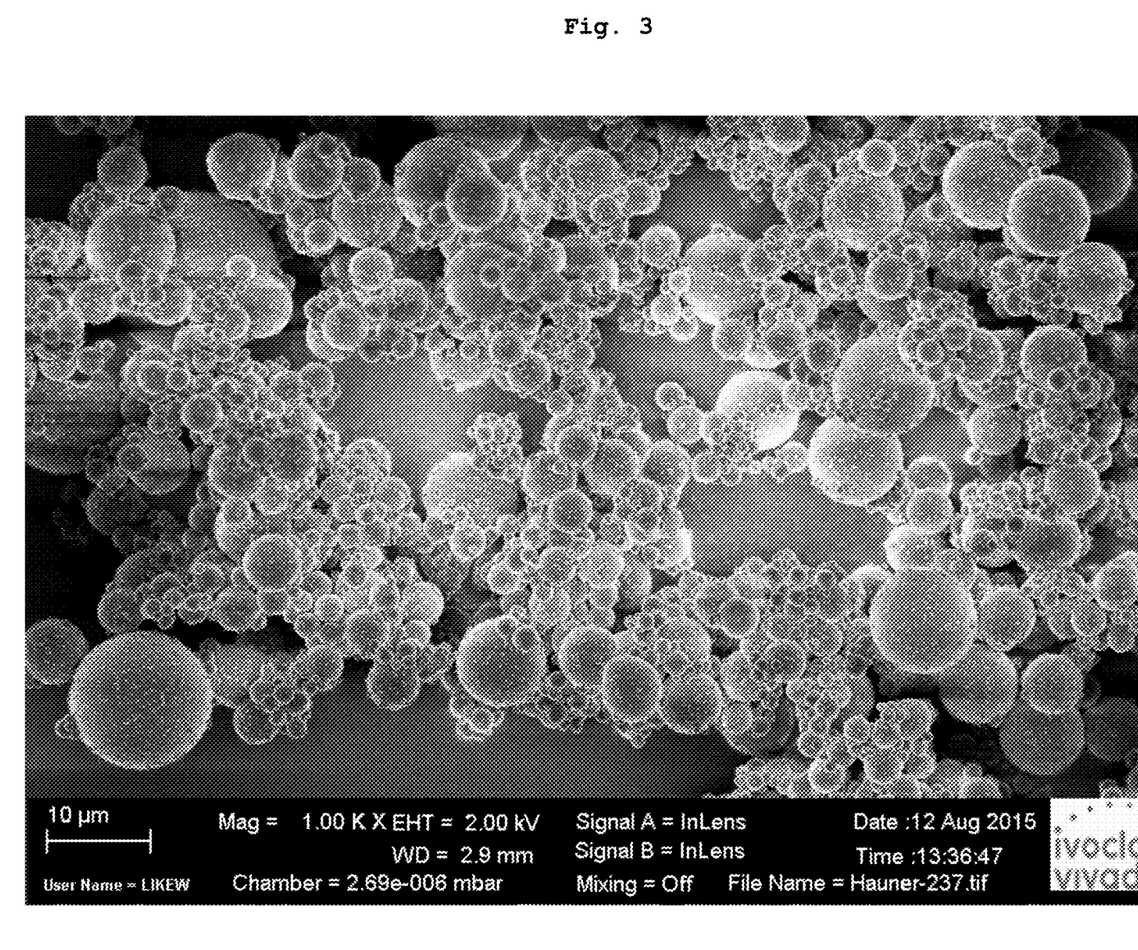
FIG. 3 shows an SEM micrograph of an accumulation of capsules according to the invention.

In FIG. 3, the SEM micrograph shows an accumulation of capsules according to the invention. The capsules have a spherical shape and have a diameter of approx. 1 μm to approx. 10 μm.

EMBODIMENT EXAMPLES

Example 1

Production of a Photochromic Fissure Sealant

The composition described in Table 1 (proportions in wt.-%) was prepared by first dissolving the initiators in the monomer mixture and then mixing the obtained solution with the fillers, dyes and the other components. Finally, the composition was homogenized using a three-roll mill.

Round test pieces (diameter 10 mm, height: 1 mm) were prepared from the compositions and were cured for 2×1 minute using a dental light source (Spectramat®, Ivoclar Vivadent AG), wherein a temporary change in color already occurred here. White test pieces were obtained, which changed color to pink when irradiated (2 s) with an LED-based light-polymerizing device ($\lambda_1$=415-465 nm). After the end of the irradiation, the test pieces decolored at room temperature within 30 s to 60 s. The alternating change in color and decoloring could also still be repeated without limitations after storage in water for 76 weeks.

TABLE 1

Composition of the material

| Function | Component | Quantity [wt.-%] |
| --- | --- | --- |
| Monomer | RM 3[1] | 40.86 |
|  | Viscoat-3PMA[2] | 24.62 |
|  | V380[3] | 11.48 |
| Initiator | Chivacure EPD[4] | 0.39 |
|  | Camphorquinone | 0.23 |

TABLE 1-continued

Composition of the material

| Function | Component | Quantity [wt.-%] |
|---|---|---|
| | BHT purum[5] (stabilizer) | 0.02 |
| | TEMPO[6] (stabilizer) | 0.01 |
| Filler | HDK 2000[7] | 4.95 |
| | Glass filler, 7 μm sil. 6.0%[8] | 14.85 |
| Dye | Edaplan 516[9] | 0.99 |
| | Color pigment Aeroxide TiO2P25[10] | 0.59 |
| | Photochromic pigment red[11] | 1.00 |

[1] Urethane dimethacrylate
[2] Tris[2-(methacryloyloxy)ethyl]phosphate
[3] Aromatic and aliphatic urethane dimethacrylate
[4] p-Dimethylaminobenzoic acid ethyl ester
[5] Butylhydroxytoluene
[6] 2,2,6,6-Tetramethylpiperidinyloxyl
[7] Pyrogenic silica (Wacker), specific surface area (BET) approx. 200 m$^2$/g
[8] Silanized glass filler G018-090 UF0
[9] Polycarboxylic acid salt (dispersant for pigments)
[10] Titanium dioxide (Evonik) with a specific surface area (BET) of approx. 50 m$^2$/g
[11] Capsules with a casing made of melamine-formaldehyde resin, which contain the dye 6'-piperidine-1,3,3,-trimethyl-spiro[indoline-2,3'-[3H]naphtho[2,1-b][1,4]oxazine] (CAS No. 114747-45-4) and methyl stearate The bending strength of the fissure sealant with the encapsulated photochromic dye was surprisingly comparable to the bending strength of a fissure sealant without encapsulated dye. A bending strength of 79±15 MPa was measured for the fissure sealant with encapsulated photochromic dye and a bending strength of 71±13 MPa was measured for the fissure sealant without encapsulated photochromic dye (in each case in accordance with ISO 4940).

Example 2

Electron Microscopic Examination of the Fissure Sealant

A platelet made of the fissure sealant described in Example 1 was produced. The production of the platelet was effected analogously to Example 1. After the curing, the surface of the platelet was polished, cleaned in an ultrasonic bath and then examined by electron microscopy. FIG. 1 shows an SEM micrograph of the edge of the casing of a ground capsule on the surface of the polished platelet. FIG. 2 shows the SEM micrograph of an empty capsule casing on the surface of the platelet. It can be seen that the edges of the capsule lie wrinkled and flexible around the photochromic dye (FIG. 1) or the edge of the cured fissure sealant (FIG. 2). The figures thus show that the capsule wall is flexible. FIG. 3 shows the photochromic capsules without matrix on an SEM carrier.

Example 3

Two-Component Dental Material

By mixing the components listed in Tables 2 and 3, a catalyst paste and a base paste were prepared. For the curing, the pastes were mixed with each other in the ratio 1:1. After the curing, the material was reversibly photochromic. The example shows that photochromic materials with high filler contents can also be prepared. Despite the high filler content, the photochromic capsules are not destroyed when the components are mixed. The pastes are particularly suitable for processing in a dual-chamber syringe.

TABLE 2

Composition of the catalyst paste

| Function | Component | Quantity [wt.-%] |
|---|---|---|
| Monomer | RM 3[1] | 22.57 |
| | Viscoat-3PMA[2] | 10.40 |
| Initiator | Cumene hydroperoxide | 1.49 |
| Stabilizer | BHT[5] | 0.07 |
| Filler | HDK 2000[7] | 2.08 |
| | Barium glass filler 1.0 μm[14] | 6.44 |
| | Silica-zirconia mixed oxide[15] | 44.95 |
| | YbF$_3$ | 11.00 |
| Dye | Photochromic pigment red[11] | 1.00 |

[1]-[11] as Table 1
[14] Silanized glass filler (CAS No. 65997-18-4)
[15] Spherosil

TABLE 3

Composition of the base paste

| Function | Component | Quantity [wt.-%] |
|---|---|---|
| Monomer | RM 3[1] | 23.40 |
| | Viscoat-3PMA[2] | 10.68 |
| Initiator | Photoinitiator K69[12] | 0.03 |
| | Hexanoyl thiourea[13] | 0.52 |
| | Copper acetylacetonate | 0.01 |
| Stabilizer | BHT[5] | 0.02 |
| | TEMPO[6] | 0.001 |
| Filler | HDK 2000[7] | 2.08 |
| | Barium glass filler 1.0 μm[14] | 6.44 |
| | YbF$_3$ | 10.89 |
| | Silica-zirconia mixed oxide[15] | 44.95 |
| Dye | Photochromic pigment red[11] | 1.00 |

[1]-[11] as Table 1
[12] Ivocerin (CAS No.: 1469766-31-1)
[13] K107 (CAS No. 41510-13-8)
[14] Silanized glass filler (CAS No. 65997-18-4)
[15] Spherosil

The invention claimed is:

1. Radically polymerizable dental material comprising at least one photochromic colorant,
   wherein the colorant is encased in a polymer capsule, the polymer capsule comprising an outer capsule wall and an inner core,
   wherein the outer capsule wall is formed of an organic polymer and the inner core comprises a liquid.

2. Dental material according to claim 1,
   wherein the outer capsule wall is formed of an organic polymer comprising melamine-formaldehyde resin, polyester, polyamide, polyurethane, polysaccharide and/or urea-formaldehyde resin.

3. Dental material according to claim 2,
   wherein the outer capsule wall is formed of the melamine-formaldehyde resin based on N-(4,6-diamino-1,3,5-triazin-2-yl)formamide (CAS No. 13236-84-5).

4. Dental material according to claim 1,
   wherein the photochromic colorant can be activated to a color change by light with a wavelength of from 350 to 800 nm.

5. Dental material according to claim 1,
   wherein the photochromic colorant can be activated to a color change by light with a wavelength of from 370 to 490 nm.

6. Dental material according to claim 1,
   wherein the photochromic colorant is a photochromic organic dye, which is selected from spirooxazines, spiropyrans, azobenzene compounds, stilbenes, pentadienyl anions and combinations thereof.

7. Dental material according to claim 6,
wherein the photochromic organic dye is a spirooxazine comprising a spirooxazine with the parent substance 1,3,3-trimethyl-spiro[indoline-2,3'-[3H]naphtho[2,1-b][1,4]oxazine (NISO) or comprising 6'-piperidine-1,3,3,-trimethyl-spiro[indoline-2,3'-[3H]naphtho[2,1-b][1,4]oxazine].

8. Dental material according to claim 1,
wherein the liquid of the inner core comprises organic solvents, carboxylic acid esters, glycerol esters and mixtures thereof.

9. Dental material according to claim 1,
wherein the liquid of the inner core comprises Miglyol, trioctanoin and/or methyl stearate.

10. Dental material according to claim 1,
further comprising one or more of a radically polymerizable monomer, an initiator for radical polymerization, and a particulate filler.

11. Dental material according to claim 10,
wherein the radically polymerizable monomer comprises a mono- or polyfunctional (meth)acrylic acid derivative and the initiator comprises a photoinitiator.

12. Dental material according to claim 10,
wherein the radically polymerizable monomer comprises at least one mono- and/or polyfunctional (meth)acrylic acid derivative, at least one non-acidic ester of phosphoric acid with a hydroxy methacrylate or a mixture thereof.

13. Dental material according to claim 1, comprising
a) 0.0001 to 5 wt.-% of at least one encapsulated photochromic colorant,
b) 0.01 to 10 wt.-% of at least one initiator,
c) optionally 5 to 85 wt.-% of at least one monomer,
d) optionally 2.5 to 80 wt.-% filler(s) and
e) optionally 2.5 to 70 wt.-% solvent,
in each case relative to the total mass of the dental material.

14. Dental material according to claim 1, comprising
a) 0.001 to 3.0 wt.-% of at least one encapsulated photochromic colorant,
b) 0.1 to 3.0 wt.-% of at least one initiator,
c) optionally 10 to 60 wt.-% of at least one monomer,
d) optionally 2.5 to 80 wt.-% filler(s) and
e) optionally 2.5 to 70 wt.-% solvent,
in each case relative to the total mass of the dental material.

15. Dental material according to claim 1, comprising
a) 0.1 to 1.0 wt.-% of at least one encapsulated photochromic colorant,
b) 0.1 to 3.0 wt.-% of at least one initiator,
c) optionally 15 to 50 wt.-% of at least one monomer,
d) optionally 2.5 to 80 wt.-% filler(s), and
e) optionally 2.5 to 70 wt.-% solvent,
in each case relative to the total mass of the dental material.

16. Dental material according to claim 11 for use as a fissure sealant.

17. Method of producing a photochromic dental material using an encapsulated photochromic colorant comprising at least one photochromic colorant, wherein the colorant is encased in a polymer capsule, the polymer capsule comprising an outer capsule wall and an inner core, wherein the outer capsule wall is formed of an organic polymer and the inner core comprises a liquid, said method comprising
mixing the photochromic colorant with one or more of a radically polymerizable monomer, an initiator for radical polymerization, and a particulate filler.

18. Method of using a dental material comprising at least one photochromic colorant, wherein the colorant is encased in a polymer capsule, the polymer capsule comprising an outer capsule wall and an inner core, wherein the outer capsule wall is formed of an organic polymer and the inner core comprises a liquid, said method comprising
using the dental material for extraoral production of a dental restoration or repair of a dental restoration,
wherein the dental restoration is cured and a conclusive assessment of coloration of the dental restoration is made.

19. Method according to claim 18,
wherein the dental restoration comprises one or more of prostheses, artificial teeth, inlays, onlays, crowns and bridges.

* * * * *